United States Patent [19]

Renga et al.

[11] 4,349,487

[45] Sep. 14, 1982

[54] PROCESS FOR FORMING ETHERS

[75] Inventors: James M. Renga; Pen-Chung Wang, both of Midland, Mich.

[73] Assignee: The Dow Chemical Company, Midland, Mich.

[21] Appl. No.: 295,428

[22] Filed: Aug. 24, 1981

[51] Int. Cl.³ .................... C07C 121/75; C07C 41/01; C07C 79/35
[52] U.S. Cl. .................................. 260/465 F; 560/61; 560/64; 568/584; 568/585; 568/586; 568/630; 568/631; 568/636; 568/639; 568/644; 568/645; 568/648
[58] Field of Search ...................... 260/465 F; 560/61; 568/585, 631, 639

[56] References Cited

PUBLICATIONS

B. Smith, Acta Chem. Scand., 10, 1006, (1956).
E. E. Smissman et al., J. Org. Chem., 37, 3944, (1972).
E. Vowinkel, Chem. Ber., 99, 1479, (1966).
S. Bittner et al., Chem. and Ind., 281, (1975).

Primary Examiner—Dolph H. Torrence
Attorney, Agent, or Firm—Douglas N. Deline

[57] ABSTRACT

Phenolic compounds are etherified by contacting at elevated temperature with a mixture of methyl trichloroacetate and either a primary alkyl halide or an aromatic halide containing strongly electron-withdrawing groups in the presence of an initiator.

10 Claims, No Drawings

PROCESS FOR FORMING ETHERS

BACKGROUND OF THE INVENTION

This invention relates to a new chemical process, more particularly to a new method for forming ethers of phenolic compounds. The resulting products obtained by the instant process have various uses as chemical intermediates, as heat transfer media, as herbicides and in other industrial applications.

In the past, aromatic ethers have been produced by alkylation of the phenoxide ion usually generated by treatment of a phenolic compound with a base such as sodium hydroxide followed by treatment with an alkyl halide, sulfate or sulfonate. The process is disfavored for commercial use because of the formation of metal salt by-products.

Alternate processes which do not form unacceptable by-products are also known. Direct alkylation of phenols by treatment with diazomethane, tetramethoxymethane or pentamethoxyphosphorane, have been previously disclosed in the art. Other processes involve treating phenol with methanol in the presence of dicyclohexylcarbodiimide or a mixture of diethylazodicarboxylate and triphenylphosphine. These processes have proven to be rather inefficient, uneconomical or ecologically unsuitable.

A suitable process for forming ethers from phenols which avoids the disadvantages of prior art methods is desired.

In our pending application Ser. No. 284,035, filed July 17, 1981, a process for methylating aromatic hydroxyl- or thiol-containing compounds by reaction with methyl trichloroacetate is disclosed.

SUMMARY OF THE INVENTION

It has now been found that phenolic compounds of the formula $Ar(OH)_x$ may be readily etherified by reaction with a mixture of methyl trichloroacetate and a suitable aryl or alkyl halide in the presence of a catalytic amount of an initiator.

DETAILED DESCRIPTION OF THE INVENTION

The phenolic compounds for use in the invented process are compounds of formula $Ar(OH)_x$, where Ar is any aromatic carbocyclic group, unsubstituted or substituted with one or more groups unreactive under the reaction conditions and x is an integer from 1 to about 3 which represents the valence of Ar.

In the above formula, a monovalent Ar can be phenyl, naphthyl, biphenylyl, or the like, unsubstituted or substituted with up to three unreactive groups. Such unreactive groups may be either electron-donating or electron-withdrawing substituents and include lower alkyl, lower alkoxy, halo, cyano, nitro, ester groups, trifluoromethyl, aralkyl and phenoxy. If n is greater than one, Ar represents the divalent or trivalent equivalents of the above, e.g., phenylene, biphenylene, naphthylylene, alkylidene diphenylene, alkylene triphenylene, oxydiphenylene, etc., also substituted or unsubstituted as described.

Preferably the phenolic compound is phenol itself or an inertly-substituted phenol.

Suitable primary alkyl halides are compounds of up to about 20 carbons of the formula $(XCH_2)_nR$ where X is chloro, bromo or iodo; n is one or two and where n is one, R is alkoxy, aryloxy, cyano, nitro, an ester group, alkyl, aryl, aralkyl, or an alkyl, aryl or aralkyl group further substituted with alkoxy, alkoxy(poly)alkyleneoxy, aryloxy, cyano, nitro or ester groups. Where n is 2, R is the corresponding alkylene, arylene, aralkylene group or such group further substituted with alkoxy, alkoxy(poly)alkyleneoxy, aryloxy, cyano, nitro or ester groups as above described. Preferred are those compounds wherein n is 1 and x is chloro.

Examples of suitable primary alkyl halides include: chloroethane, 1-bromohexane, 1-chlorododecane, chloroacetonitrile, 1-chloro-2-methoxyethane, chloromethoxyethoxymethane, 1-chloro-3-nitropropane, methyl chloromethylacetate, ethyl chloromethylacetate, phenyl chloromethylacetate, benzyl chloride, benzyl bromide, 1-chloro-2-phenoxypropane and the like.

Suitable aromatic halides are compounds of up to about 20 carbons of the formula $R'-(X)_m$ where $R'$ is an aromatic group containing at least one benzene ring structure substituted with at least one strongly electron-withdrawing group. X is a chloro, bromo or iodo moiety covalently bonded to the benzene ring structure in a position ortho or para to the strongly electron-withdrawing group and m is one or two. Suitable strongly electron-withdrawing groups include cyano, nitro, trifluoromethyl or trichloromethyl. Preferred are those aromatic halides wherein X is chloro and m is one. Most preferred are monochlorinated benzenes containing two strongly electron-withdrawing groups present in positions ortho or para to X.

In the invented process, the phenolic compound is contacted with methyl trichloroacetate and the aromatic or alkyl halide in a suitable reactor vessel. Generally, reactors of ordinary design and construction may be employed. The reactants are combined in any order and reacted at an elevated temperature from about 100° C. to about 180° C. Preferred temperatures are from about 110° C. to about 150° C. Generally, the reaction is conducted under atmospheric pressure although elevated or reduced pressures may also be employed if so desired. Where volatile alkyl halides are present, elevated pressures must be employed to retain all reactants in solution.

The reactants may be combined in any ratio, however, generally about stoichiometric amounts of all three reactants are employed to limit contamination of the product with unreacted starting materials. Preferred equivalent ratios of phenolic compound to methyl trichloroacetate are from about 1:1 to 1:2. Preferred equivalent ratios of phenolic compound to aromatic or alkyl halide compound are from about 1:1 to 1:2.

The reaction is initiated by the presence of one of several suitable initiators. Basic catalysts, such as alkali metal alkoxides, salts of a strong base and a weak acid, or non-nucleophilic organic bases are suitable. The latter class consists in practice of tertiary amines, both aliphatic and aromatic. Suitable basic catalysts include triethylamine, tributylamine, pyridine, quinoline, N,N-dimethylaminopyridine, alkali metal carbonates, acetates and alkoxides. Additional suitable initiators include stable quaternary salts such as ammonium or phosphonium quaternary salts having inert counterions. Preferably, these salts have the general formula (R")₄AY where each R" is a hydrocarbon moiety, A is a quaternary nitrogen or phosphorus atom, and Y is an inert (i.e., unreactive in this process) neutralizing anion which may be inorganic, e.g., chloride, bromide, iodide, bicarbonate, sulfate, or the like, or Y may be an organic ion such as formate, acetate, benzoate, phenate, or bisphenate. The R" groups may be alkyl, aryl, alkaryl, aralkyl, or cycloalkyl. Also two R" groups may combine to form a heterocyclic ring. Illustrative quaternary salt catalysts are tetrabutylammonium iodide, benzyltriethylammonium chloride, N-methylpyridinium chloride, N,N-dibutylmorpholinium iodide, N-propylpyrrolium chloride, tetrabutylphosphonium bromide, tributylmethylphosphonium formate, tetrapropylphosphonium bisulfate, and similar ammonium and phosphonium salts with these and other such inorganic and organic neutralizing anions as described above. The catalytic salt may be added as such to the reaction mixture or it may be formed in situ.

It is believed the various initiator compounds operate according to different mechanisms. For example, basic catalysts are believed to react with the aromatic hydroxyl- or thiol-containing reactant, deprotonating the reactant and thereby producing a species capable of demethylating methyl trichloroacetate. Quaternary salts on the other hand, appear to activate methyl trichloroacetate directly providing an active species able to react with the aromatic compound.

The quantity of initiator compound is not critical so long as any significant amount is present and available at the reaction site. Suitably from about 0.1–1 percent of initiator based on the weight of the reactants is used. Larger amounts of initiator may be employed but may complicate the ability to produce pure product.

The initiator should be at least partially soluble in the reaction mixture and it may be advantageous in accomplishing this goal to employ an additional agent to render the initiator soluble in the reaction medium. Suitable agents, referred to hereinafter as "solubilizing agents", which are particularly suitable for use with basic catalysts include the compounds generally known as phase-transfer catalysts such as, for example, cyclic oligomers of ethylene oxide known as crown ethers. Such solubilizing agents may be employed in minor amounts, for example, in the ratio of about 0.005–1.0 mole per mole of basic catalyst.

A reaction solvent is usually not required or desirable, but use of a solvent may be advantageous under some conditions, e.g., when low boiling reactants or solid reaction products are involved. Excess methyl trichloroacetate can be used as the solvent if desired. Polar solvents appear to increase the rate of reaction. Relatively high boiling inert solvents such as N,N-dimethylformamide, sulfolane, dimethylsulfoxide, glycol diethers, and substituted aromatics such as anisole, o-dichlorobenzene, alkylated pyridines, and the like are suitable.

In the usual operation of the process the reactants and initiator are combined in a reactor as previously described. Suitably the reactor is provided with a distillation head or other means to remove the volatile reaction by-products, chloroform, carbon dioxide and methyl halide formed during the course of the reaction. The by-products distill off substantially as formed and provide a useful indication of the course of the reaction. Because the by-products may themselves be commercially valuable, they may be collected as condensate in a suitable receiver. A stream of nitrogen or other inert purging gas may be employed to aid in removing volatile reaction products.

The reaction proceeds rapidly and generally is completed in from about 1 to about 5 hours depending of course on the amounts of reactants, temperature and other reaction conditions. The product is the corresponding alkyl or aryl ether of the phenolic compound. The products are recovered from the reaction vessel and separated from residual initiator compound if desired by ordinary techniques such as distillation.

SPECIFIC EMBODIMENTS

Having described the invention, the following examples are provided as further illustrative and are not to be construed as limiting the invention.

EXAMPLE 1

A mixture of phenol (2.35 g, 0.025 mole), methyl trichloroacetate (5.32 g, 0.03 mole), benzyl chloride (3.18 g, 0.025 mole), potassium carbonate catalyst (0.069 g, 0.0005 mole) and 18-crown-6 cyclic polyether (0.132 g, 0.0005 mole) was heated in a 25-ml glass round-bottom flask fitted with a distillation head and stirrer. The mixture was heated to 150° C. Gas evolution was observed to commence at about 110° C. The reaction was continued until no additional liquid was collected in the dry ice receiver. Analysis of the reactor contents by nuclear magnetic resonance spectroscopy and gas-liquid chromatography indicated substantially complete conversion of phenol to benzyl phenyl ether. Product recovery by distillation gave 83 percent purified yield.

EXAMPLES 2–13

The procedure of Example 1 was substantially repeated excepting that the phenolic compounds and alkyl or aromatic halides further identified in Table I were employed. Product identity and purified yields are provided in Table I.

TABLE I

| Example | Phenolic Compound | Halide | Product | % Yield |
|---|---|---|---|---|
| 2 | phenol | benzyl bromide | benzyl phenyl ether | 91 |
| 3 | 3,5-dimethylphenol | benzyl chloride | benzyl 3,5-dimethylphenyl ether | 75 |
| 4 | 4-methoxyphenol | benzyl chloride | benzyl 4-methoxyphenyl ether | 72 |
| 5 | 2-chlorophenol | benzyl chloride | benzyl 2-chlorophenyl ether | 85 |
| 6 | 4-chlorophenol | methyl chloromethyl acetate | methyl (4-chlorophenoxy) acetate | 77 |
| 7 | 4-chlorophenol | ethyl chloromethylacetate | ethyl (4-chlorophenoxy) acetate | 80 |
| 8 | 2,4-dichlorophenol | ethyl chloromethylacetate | ethyl (2,5-dichlorophenoxy) acetate | 81 |
| 9 | phenol | chloroacetonitrile | phenoxy acetonitrile | 81 |
| 10 | 2,4-dichlorophenol | chloroacetonitrile | (2,4-dichlorophenoxy) acetonitrile | 75 |
| 11 | 3-methylphenol | 2-nitro-4-trifluoromethylphenyl chloride | 3-methylphenyl-2-nitro-4-trifluoromethyl phenyl ether | 66 |
| 12 | 2,4-dichlorophenol | 2-cyano-4-trifluoromethyl- | 2,4-dichlorophenyl 2-cyano-4-tri- | 73 |

TABLE I-continued

| Example | Phenolic Compound | Halide | Product | % Yield |
|---|---|---|---|---|
| 13 | 2,4-dichloro-phenol | phenyl chloride 2-nitro-4-trifluoromethylphenyl chloride | fluoromethyl-phenyl ether 2,4-dichloro-phenol 2-nitro-4-trifluoromethyl-phenyl ether | 72 |

What is claimed is:

1. A process for forming ethers of phenolic compounds comprising contacting a phenolic compound of the formula $Ar(OH)_x$ with methyl trichloroacetate and either a primary alkyl halide or an aromatic halide in the presence of a catalytic amount of an initiator at a temperature from about 100° C. to about 180° C. wherein:

Ar is any aromatic carbocyclic group of valence x;

x is an integer from one to about three;

the primary alkyl halide is a compound of up to about 20 carbons of the formula $(XCH_2)_nR$ where:

X is chloro, bromo or iodo;

n is one or two; and when n is one, R is an alkoxy, aryloxy, cyano, nitro, ester, alkyl, aryl or aralkyl group, or an alkyl, aryl or aralkyl group further substituted with alkoxy, polyalkoxy, aryloxy, cyano, nitro or ester groups; and when n is two, R is alkylene, arylene, aralkylene, or such groups further substituted with alkoxy, alkoxy(poly)alkyleneoxy, aryloxy, cyano, nitro or ester groups; and the aromatic halide is a compound of up to about 20 carbons of the formula $R'-(X)_m$ where:

R' is an aromatic group containing at least one benzene ring structure substituted with at least one strongly electron-withdrawing group located ortho or para to X;

X is previously defined; and m is one or two.

2. The process of claim 1 wherein the phenolic compound is phenol or an inertly-substituted phenol.

3. The process of claim 1 wherein the initiator is either a basic catalyst selected from the group consisting of alkali metal alkoxides, salts of strong bases and weak acids, and non-nucleophilic organic bases or a quaternary ammonium or phosphonium salt.

4. The process according to claim 2 wherein the initiator comprises a basic catalyst and a solubilizing agent.

5. The process according to claim 4 wherein the basic catalyst is an alkali metal carbonate and the solubilizing agent is a cyclic polyether.

6. The process according to claim 1 wherein the temperature is from about 110° C. to about 150° C.

7. The process according to claim 1 wherein a primary alkyl halide is employed.

8. The process according to claim 7 wherein X is chloro and m is one.

9. The process according to claim 1 wherein an aromatic halide is employed.

10. The process according to claim 9 wherein the aromatic halide is a monochlorinated benzene additionally containing two strongly electron-withdrawing groups located ortho or para to the chlorine.

* * * * *

UNITED STATES PATENT AND TRADEMARK OFFICE
CERTIFICATE OF CORRECTION

PATENT NO. : 4,349,487
DATED : September 14, 1982
INVENTOR(S) : James M. Renga and Pen-Chung Wang It is certified that error appears in the above—identified patent and that said Letters Patent is hereby corrected as shown below:

Column 3, line 8, "Also two R" groups" should read -- Also, two R" groups --.

Column 3, line 31, "about 0.1-1 percent" should read -- about 0.01-1 percent --.

Signed and Sealed this

Twenty-eighth Day of December 1982

[SEAL]

Attest:

GERALD J. MOSSINGHOFF

Attesting Officer   Commissioner of Patents and Trademarks